United States Patent [19]
Persson

[11] Patent Number: 5,927,100
[45] Date of Patent: Jul. 27, 1999

[54] FREEZER FOR A LIQUID

[75] Inventor: Per-Oskar Persson, Helsingborg, Sweden

[73] Assignee: Ingenjörsfirman Per-Oskar Persson AB, Helsingborg, Sweden

[21] Appl. No.: 09/132,498

[22] Filed: Aug. 11, 1998

Related U.S. Application Data

[63] Continuation of application No. PCT/SE97/00221, Feb. 13, 1997.

[30] Foreign Application Priority Data

Feb. 13, 1996 [SE] Sweden .................................. 9600508

[51] Int. Cl.$^6$ ...................................................... F25C 1/06
[52] U.S. Cl. ............................... 62/356; 249/79; 249/117
[58] Field of Search ............................ 62/66, 340, 356; 249/79, 117

[56] References Cited

U.S. PATENT DOCUMENTS

| | | | |
|---|---|---|---|
| 3,480,015 | 11/1969 | Gonzalez | 128/276 |
| 3,586,097 | 6/1971 | Bender | 165/17 |
| 3,940,232 | 2/1976 | Stock | 62/356 |
| 4,537,034 | 8/1985 | Crouch | 62/62 |
| 4,587,810 | 5/1986 | Fletcher | 62/340 |
| 4,601,174 | 7/1986 | Wilson | 62/66 |
| 5,297,234 | 3/1994 | Harms et al. | 392/470 |

FOREIGN PATENT DOCUMENTS 2 014 583  8/1979  United Kingdom .

*Primary Examiner*—William E. Tapolcai
*Attorney, Agent, or Firm*—Browdy and Neimark

[57] ABSTRACT

A freezer for a liquid in a receptacle (14) comprises a housing (1), containing a cooling battery (5) for cooling a gas, a means (7) for generating a flow of the cooled gas and a jet device. The latter comprises a plurality of shells (6), each completely surrounding a receptacle (14) inserted into the respective shells with the exception of a first opening (15) for inserting the receptacle and a second opening (16) for discharging a flow of gas resulting from jets directed towards the outside of the receptacle. Each shell (6) has holes (18) in all its side walls in areas directly opposite a receptacle inserted into the shell for directing jets towards the outside of the receptacle. In addition, the freezer has indicators (11) for indicating which shells (6) do not contain a receptacle (14) and for indicating when the liquid in a receptacle inserted into a shell is frozen.

10 Claims, 3 Drawing Sheets

FIG.3
FIG.4
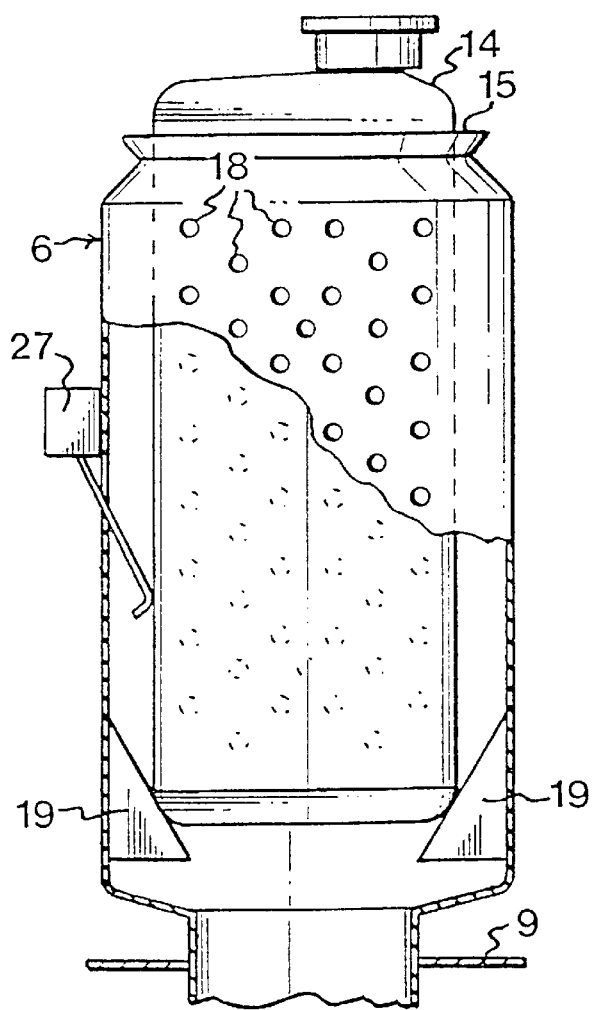
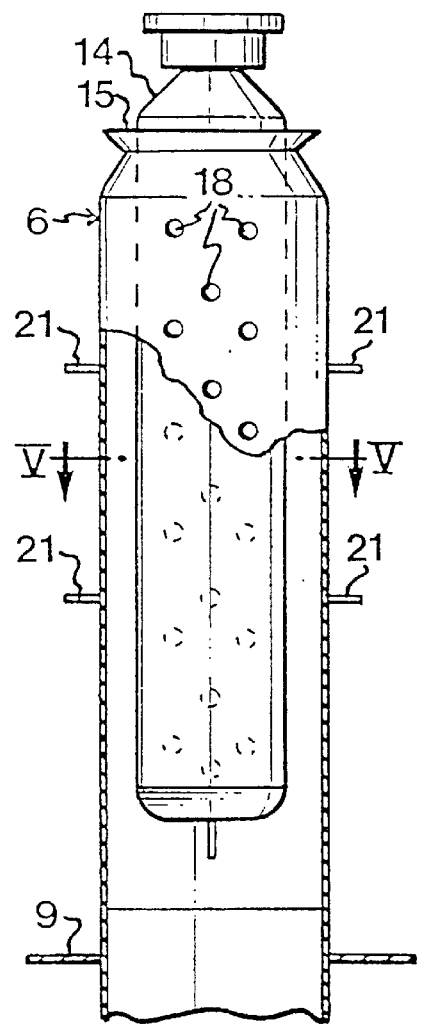

FREEZER FOR A LIQUID

This application is a continuation of copending parent application no. PCT/SE97/00221, filed Feb. 13, 1997.

The present invention generally relates to a freezer for a liquid in a receptacle and particularly to a freezer for blood plasma. More precisely, the present invention relates to a freezer comprising a housing, which contains a cooling battery for cooling a gas, a means for generating a flow of the cooled gas, and a device for generating jets of the flow of the cooled gas which are directed towards the outside of the receptacle.

It is known from experience that blood plasma should be frozen as soon as possible after being drawn. The freezing process itself should occur quickly enough for the plasma to reach a temperature of about −30° C. within an hour. After freezing, the plasma is normally stored at a temperature of about −70° C. while awaiting transportation to, for example, a processing facility.

Previously, the plasma was stored either in plastic bags or in round plastic bottles during freezing. Recently, rather than using round plastic bottles, it has become common to use essentially parallelepipedal plastic receptacles, so-called vials, for handling plasma from the drawing location to the processing location. These vials have a rectangular cross-section measuring about 40×100 mm. Because the vials are as thin as 40 mm, it has become possible to lower the temperature of the plasma at the desired rate without having to resort to extremely low cooling temperatures, such as those obtained from liquid nitrogen.

In a first method for freezing the plasma, the plasma-filled receptacles have been lowered into an alcohol bath with a temperature of about −40° C. In order to speed up the freezing process, the alcohol is caused to circulate in the bath.

In a second method for freezing the plasma, the plasma-filled receptacles are placed in metal blocks having holes with the same cross-sectional shape as the receptacles. In addition, the metal blocks have channel systems, in which a cooling medium is circulating.

A third, recently developed, method for freezing the plasma utilises several plastic shells with flexible walls. When a certain number of plasma-filled receptacles are in place, each in its own plastic shell, the pressure in a liquid surrounding them is increased, so that good contact is achieved between the liquid and the plasma-filled receptacles. The surrounding liquid is also used as a cooling medium.

The first method is environmentally dangerous and may cause fire because alcohol is used as a cooling medium. The second method provides relatively poor thermal transmittance from the receptacles to the metal block and, in addition, the receptacles tend to freeze to the holes of the metal block. The third method requires a comparatively complicated freezer and also requires that, on each freezing occasion, every plastic shell contains a receptacle before the freezing can start.

Yet another method, which obviates some of the drawbacks of the three methods described above, is disclosed in U.S. Pat. No. 5,297,234. In this method, cold air jets are generated and directed towards a specially formed blood receptacle. However, the device used for carrying out the method is of complicated construction, as is the blood receptacle used, and leads to hygienic risks, poor efficiency, and poor adaptability to conventionally utilised receptacles or bags for primarily blood or blood components.

A first object of the invention is to enable the freezing of a liquid in a receptacle without the drawbacks of the known methods, i.e. in a simple and environmentally friendly process, particularly with the possibility of utilising blood receptacles or blood bags, and without any hygiene risk or risk of the receptacle freezing and getting stuck.

A second object of the invention is to enable the freezing of the liquid in one receptacle essentially independently of the freezing of the liquid in another receptacle, i.e. in a freezer according to the invention, it should be possible to insert and remove the receptacles individually and at any time during the operation of the freezer.

The first object is achieved by the freezer according to the invention having the features stated in the appended claim 1.

The fact that cold air jets of sufficient air speed provide a sufficiently high heat transfer coefficient at the surface of the receptacle is thus utilised to meet the basic requirement of rapid freezing, i.e. within about 60 minutes, to a predetermined temperature, preferably −30° C.

In order to make the process economically viable, the air is suitably recirculated via the cooling battery. In particular, if the liquid consists of blood plasma, a heat transfer coefficient at the receptacle surfaces concerned may need to be larger than 100 $W/m^{2 \cdot \circ}$ C. but does not need to be larger than 200 $W/m^{2 \cdot \circ}$ C., which is achieved according to the invention by the air speed being adjusted accordingly.

However, it has to be emphasised that the heat transfer coefficient does not have to be larger than is necessary for it to be optimised in relation to the thermal conduction resistance of the liquid, particularly the blood plasma. However, since the preferred receptacles are relatively thin, the thermal conduction resistance of the liquid is of limited importance. In general, the optimisation implies that the heat transfer coefficient does not need to be made larger than necessary for the thermal conduction in the liquid to become the limiting factor for the rapid cooling of the liquid.

In the freezer according to the invention, the jet device comprises a plurality of shells, each completely surrounding a receptacle inserted into each shell with the exception of a first opening for inserting the receptacle and a second opening for discharging the flow of gas resulting from the jets which are directed towards the outside of the receptacle, and each shell having holes in all its side walls in areas directly opposite a receptacle inserted into the shell, i.e. distributed over essentially the whole surface of the shell between the first opening and the second opening, for directing the jets towards the outside of the receptacle.

Because air is used as a cooling medium, the freezer is very simple, reliable in service, and environmentally friendly.

In the preferred embodiment of the freezer according to the invention, each shell has a valve for increasing the cross-section of the second opening when a receptacle is being inserted into the shell, so that the air resistance through each shell is essentially independent of whether the shell contains a receptacle or not. As a result of this construction, the cooling of a receptacle in a shell in the freezer will be effected in the same way whether the other shells in the freezer contain receptacles or not. Thus, it will be possible to remove a receptacle from the freezer as soon as the liquid in the receptacle has reached the desired temperature, without the cooling of other possible receptacles in the freezer being affected.

For monitoring purposes the freezer according to the invention may suitably have an indicator for indicating with respect to each shell whether it is empty or contains a receptacle, and, in the latter case, for indicating when the receptacle has been in the shell for a predetermined period of time and thus has reached a certain temperature. Alternatively, a directly temperature-sensitive indicator may be used.

The invention will now be described in more detail with reference to the accompanying drawings, in which:

FIG. 3 is a front view of one of several shells for one receptacle each, which are part of the freezer according to FIGS. 1 and 2, FIG. 4 is a side view of the shell in FIG. 3.

Figure 1:
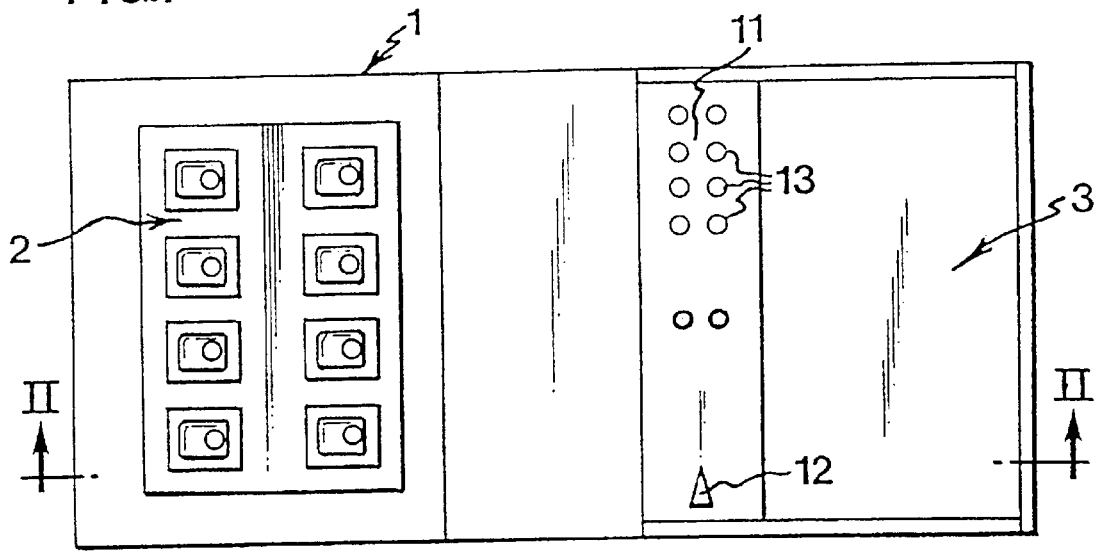
FIG. 1 is a top view of an embodiment of a freezer according to the invention.
Figure 2:
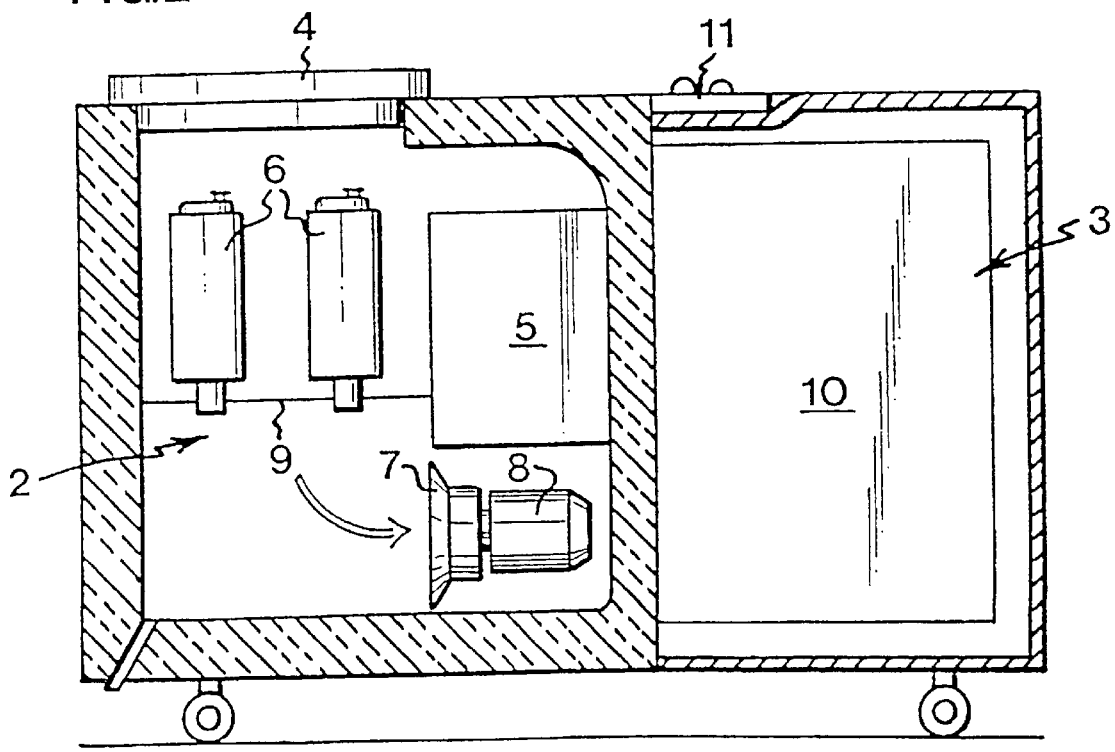
FIG. 2 is a cross-sectional view along the line II—II in FIG. 1.
Figure 5:
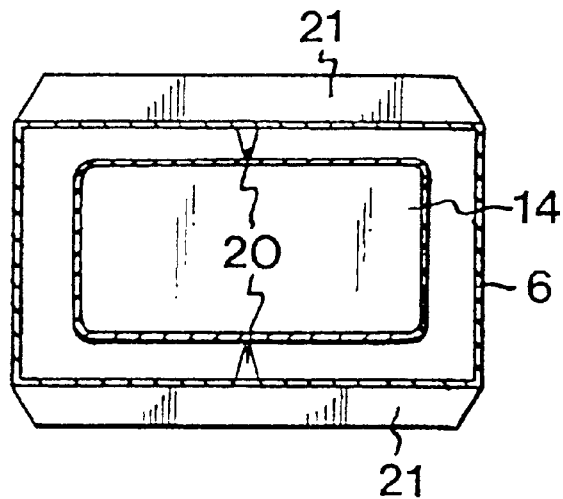
FIG. 5 is a cross-sectional view along the line V—V in FIG. 4.

The embodiment shown in FIGS. 1 and 2 of a freezer according to the invention comprises a housing 1 with a first chamber 2, which is heat-insulated, and an adjacent chamber 3, which does not have to be heat-insulated but may advantageously be soundproof. A cover 4, which is also heat-insulated, seals an opening into the chamber 2, which contains a cooling battery 5, a plurality of shells 6, and a fan 7 with a fan motor 8. The shells 6 are installed in a partition wall 9 in such a way that the fan 7 circulates the air in the chamber 2 through the cooling battery 5 and thence through each of the shells 6 back to the fan 7.

The cooling battery 5 is part of a refrigerating machine 10, which is contained in the chamber 3 and which is of a conventional type with a compressor and a condenser. The latter may advantageously be water-cooled, which results in a low sound level and no heat emission to the space where the freezer is located.

A control panel 11 with a change-over switch 12 for turning on and turning off the current to the freezer and several indicator lights 13 are located on the top of the freezer.

A shell 6 will now be described in more detail with reference to FIGS. 3–6. These figures show a shell 6 and a receptacle 14 or a vial of the type that is now usually used for freezing blood plasma. The receptacle 14 is essentially parallelepipedal and measures approximately 40×100×250 mm and is usually made of plastic.

The shell 6 has the form of a sleeve with a first opening 15 at its upper end, the opening 15 having essentially the same cross-sectional dimensions as the receptacle 14 or at least as the upper part of the receptacle, so that when a receptacle 14 is inserted into the shell 6, the opening 15 is practically completely sealed. Furthermore, the shell 6 has a second opening 16 at its lower end. This single second opening 16 contains a valve 17 shown in FIG. 6.

The shell 6 has somewhat larger cross-sectional dimensions than the receptacle 14, so that a free space is formed between the outside of the receptacle 14 and the inside of the shell 6. In each side wall of the shell 6, there are several holes 18 in areas directly opposite a receptacle 14 inserted into the shell 6. Furthermore, the shell 6 is fixedly attached to the partition wall in such a way that air can flow from one side of the partition wall 9 to the other side through the shell 6 only.

In its inserted position in the shell 6, the receptacle 14 is kept in place partly by two shoulders 19, against which the lower end of the receptacle 14 abuts, partly by the opening 15 itself. Two vertical bars 20 are also fixedly attached to the inside of the shell 6 opposite each other in order to abut against the two wider sides of the receptacle 14. As a result, the receptacle 14 is prevented from expanding in connection with the freezing of a liquid inside it. For the same reason, the shell 6 may have exterior horizontal reinforcement bars 21 on the same walls as the vertical reinforcement bars 20.

Figure 6:
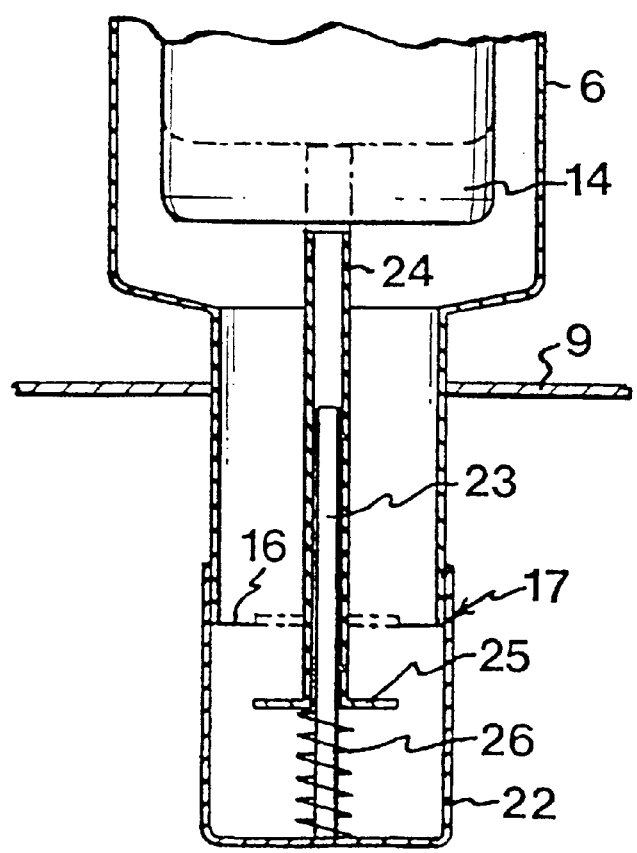
FIG. 6 is a cross-sectional view of a valve associated with each shell.

The valve 17 shown in more detail in FIG. 6 comprises a U-shaped clamp 22, whose legs are fixedly connected to the lower end of the shell 6. A rod 23 is fixedly attached to the clamp 22 and extends into the second opening 16 of the shell 6. A tubular piece 24, which is closed at the top, is pushed down over the rod 23 and is displaceable up and down over it. At its lower end the tubular piece 24 has a plate 25, and between the plate 25 and the clamp 22 there is a helical compression spring 26.

When there is no receptacle 14 inserted into the shell 6, the plate 25 is pressed up into the second opening by the compression spring 26. However, when a receptacle 14 is inserted in the shell 6, the bottom of the receptacle 14 presses the tubular piece 24 down, so that the plate 25 is pressed down under the second opening 16. The size of the cross-section of the opening 16 will thus vary depending on whether the shell 6 contains a receptacle 14 or not. The difference between these cross-sections is determined so that the air resistance through the shell 6 is independent of whether there is a receptacle 14 in the shell 6 or not.

As is shown in FIG. 3, the shell 6 may have a transducer 27, e.g. a microswitch, which will indicate whether the shell 6 contains a receptacle 14 or not. In this case, there can be an indicator light 13 for every shell 6, indicating whether the shell 6 is empty or whether it contains a receptacle 14. The freezer according to the invention may also comprise timing circuits, which cause the indicator light 13 of each shell, for instance, to blink when a receptacle 14 has been in the shell 6 for a predetermined length of time, which has been determined to be sufficient for the freezing of the liquid in the receptacle 14 to the intended temperature.

The freezer according to the invention may also comprise a transducer for the temperature in the chamber 2 and a corresponding indicator or indicator light on the control panel 11. In this way, the operator can get the go-ahead for using the freezer. The freezer may also contain a pressure transducer on each side of the partition wall 9 and a corresponding indictor or indicator light on the control panel 13 for indicating that there is sufficient pressure difference, so that the speed of the air which passes through the holes 18 in one of the shells 6 with a receptacle 14 inserted will be high enough for the required heat transfer coefficient to be achieved at the external surface of the receptacle 14. Finally, the freezer may also advantageously comprise a switch, which switches off the fan motor 8 when the cover 4 is opened, so that cooled air does not pass unnecessarily out of the chamber 2.

When the change-over switch 12 has been turned and the freezer according to the invention is ready to be used, as indicated by the indication on the control panel 11 of a sufficiently low temperature inside the chamber 2 and a sufficient pressure drop over the partition wall 9, an arbitrary number of receptacles 14 may be placed each in its own shell 6, after which the chamber 2 is sealed with the cover 4. During the treatment time for receptacles 14 which have previously been inserted, further receptacles 14 may be inserted if empty shells 6 are available, which will be indicated on the control panel 11. As soon as a receptacle 14 has been in the freezer for the required period of time, this will be indicated on the control panel and the receptacle 14 may then be removed immediately and replaced by a new receptacle 14. By virtue of the valve 17 on each shell 6, the treatment of a receptacle 14 in a shell 6 will be independent of whether the other shells 6 in the freezer contain a receptacle 14 or not.

Normally, the receptacles 14 are slightly cone-shaped, i.e. they become somewhat narrower towards the bottom. As a result of the vertical reinforcement bars 20, the receptacle 14 will keep its shape during the freezing, and thus the slightly conical shape facilitates the removal of the receptacle 14 from the shell 6.

The freezer according to the invention is also easily adaptable to various kinds of receptacles, shape-permanent ones, e.g. plastic bottles, as well as flexible ones, e.g. plastic bags. For example, the shells 6 or at least their upper parts, preferably above the partition wall 9, can be made removable and therefore exchangeable for adaptation to receptacles of various shapes. By the use of air-permeable cases, whose shape corresponds to that of the receptacles 14 and which therefore fit into the shells 6, liquids can be frozen in plastic bags, which can be placed each in its own case. These cases may consist of plastic or metal, e.g. a metal net, and be designed to remain in the respective shells 6 or even be permanently connected to their own shell 6, in which case only the plastic bag is inserted or removed. Alternatively, they may be designed to be inserted into the shell 6 and removed from the shell with the plastic bag.

The adaptability described above also makes it possible in the freezer according to the invention to utilise the type of receptacles which are normally used for the current liquid in a processing step previous or subsequent to the freezing, so that the re-drawing of the liquid may be avoided.

It will be appreciated that the embodiment of the freezer according to the invention described above can be modified in a number of respects within the scope of the protection defined in the appended claims. Thus, the invention is, for example, not limited to air only, but other gases may also be utilised.

I claim:

1. A freezer for a liquid in a receptacle (14), comprising a housing (1), which contains a cooling battery (5) for cooling a gas, a means (7) for generating a flow of the cooled gas and a device for generating jets of the flow of the cooled gas, which are directed towards the outside of the receptacle (14), characterised in that the jet device comprises a plurality of shells (6), each completely surrounding a receptacle (14) inserted into it with the exception of a first opening (15) for insertion of the receptacle and a second opening (16) for discharging the flow of gas resulting from the jets directed towards the outside of the receptacle, and each shell having holes (18) in all its side walls in areas directly opposite a receptacle inserted into the shell for directing the jets towards the outside of the respective receptacles.

2. A freezer as set forth in claim 1, characterised in that each shell (6) has a valve (17) for increasing the cross-section of the second opening (16) in connection with the insertion of a receptacle (14) into the shell (6), so that the flow of gas through each shell is essentially independent of whether the shell contains a receptacle or not.

3. A freezer as set forth in claim 1, characterised in that the first opening (15) becomes substantially sealed by a receptacle (14) inserted into it.

4. A freezer as set forth in claim 1, wherein the receptacle (14) has an essentially rectangular cross-section, characterised in that each shell (6) has reinforcement bars (20) for abutting against the opposite wide sides of the receptacle (14).

5. A freezer as set forth in claim 2, characterised by an indicator (13) for indicating for each shell (6) whether it is empty or contains a receptacle (14), and in the latter case, for indicating when the receptacle has been in the shell for a predetermined period of time.

6. A freezer as set forth in claim 1, characterised by a means for turning off the means (7) for creating the flow of gas during the insertion of a receptacle (14) into the freezer or the removal of a receptacle from the freezer.

7. A freezer as set forth in claim 1, characterised by a temperature transducer for the air cooled by the cooling battery (5) and an indicator for indicating when a predetermined temperature has been achieved.

8. A freezer as set forth in claim 1, characterised by a pressure transducer for the pressure drop over the shell (6) for indicating when a predetermined pressure drop has been achieved.

9. A freezer as set forth in claim 1, characterised by an air-permeable case, into which a plastic bag containing a liquid is insertable and which case is in turn insertable into at least one of the shells (6) as a receptacle.

10. A freezer as set forth in claim 1, characterised in that least one of the shells (6) is completely or partially removable from the housing for being exchanged for another shell.

* * * * *